(12) United States Patent
Jones et al.

(10) Patent No.: US 7,668,736 B2
(45) Date of Patent: *Feb. 23, 2010

(54) INTEGRATED EMERGENCY MEDICAL TRANSPORTION DATABASE AND VIRTUAL PRIVATE NETWORK SYSTEM

(75) Inventors: Scott J. Jones, Escondido, CA (US); Rany Polany, Escondido, CA (US); Kevin C. Hutton, Solana Beach, CA (US)

(73) Assignee: Golden Hour Data Systems, Inc., San Diego, CA (US)

( * ) Notice: Subject to any disclaimer, the term of this patent is extended or adjusted under 35 U.S.C. 154(b) by 964 days.

This patent is subject to a terminal disclaimer.

(21) Appl. No.: 10/012,884

(22) Filed: Nov. 6, 2001

(65) Prior Publication Data

US 2007/0203742 A1  Aug. 30, 2007

Related U.S. Application Data

(60) Provisional application No. 60/246,307, filed on Nov. 6, 2000.

(51) Int. Cl.
*G06F 19/00* (2006.01)

(52) U.S. Cl. .............................................. 705/3; 705/2

(58) Field of Classification Search ................. 705/2–3; 600/300; 455/553
See application file for complete search history.

(56) References Cited

U.S. PATENT DOCUMENTS

| | | | |
|---|---|---|---|
| 1,873,126 A | 8/1932 | Hugershoff | |
| 2,977,177 A | 3/1961 | McLaughlin et al. | |
| 3,921,318 A | 11/1975 | Calavetta | |
| 4,221,404 A | 9/1980 | Shuffstall | |
| 4,236,332 A | 12/1980 | Domo | |
| 4,814,711 A | 3/1989 | Olsen et al. | |
| 4,819,053 A | 4/1989 | Halavais | |
| 4,858,121 A | 8/1989 | Barber et al. | |
| 5,122,959 A | 6/1992 | Nathanson et al. | |
| 5,146,439 A | 9/1992 | Jachmann et al. | |
| 5,283,829 A | 2/1994 | Anderson | |
| 5,327,341 A | 7/1994 | Whalen et al. | |
| 5,465,206 A | 11/1995 | Hilt et al. | |
| 5,483,443 A | 1/1996 | Milstein et al. | |

(Continued)

FOREIGN PATENT DOCUMENTS

JP    01319861 A    12/1989

(Continued)

OTHER PUBLICATIONS

Public Law 104-191, Health Insurance Portability and Accountability Act of 1996, published Aug. 21, 1996, located at <http://aspe.hhs.gov/admnsimp/pl 104191.htm>.*

(Continued)

*Primary Examiner*—Robert W Morgan
(74) *Attorney, Agent, or Firm*—Manuel F. de la Cerra

(57) ABSTRACT

A system and method for providing secure data communications and user access authorization for an integrated emergency medical transportation database. The secure communications and user authorization is provided by a Virtual Private Network ("VPN"), allowing confidential patient medical records to be transmitted via a public network such as the Internet without compromising the confidentiality of the data.

44 Claims, 6 Drawing Sheets

U.S. PATENT DOCUMENTS

| | | | |
|---|---|---|---|
| 5,508,912 | A | 4/1996 | Schneiderman |
| 5,544,044 | A | 8/1996 | Leatherman |
| 5,550,976 | A | 8/1996 | Henderson et al. |
| 5,619,991 | A | 4/1997 | Sloane |
| 5,734,706 | A | 3/1998 | Windsor et al. |
| 5,761,278 | A | 6/1998 | Pickett et al. |
| 5,805,670 | A | 9/1998 | Pons et al. |
| 5,867,821 | A * | 2/1999 | Ballantyne et al. ............. 705/2 |
| 5,874,897 | A | 2/1999 | Klempau et al. |
| 5,900,883 | A | 5/1999 | Crucs |
| 5,911,132 | A | 6/1999 | Sloane |
| 5,940,013 | A | 8/1999 | Vladimir et al. |
| 5,974,355 | A | 10/1999 | Matsumoto et al. |
| 6,029,144 | A | 2/2000 | Barrett et al. |
| 6,044,323 | A | 3/2000 | Yee et al. |
| 6,106,459 | A | 8/2000 | Clawson |
| 6,117,073 | A | 9/2000 | Jones et al. |
| 6,151,581 | A | 11/2000 | Kraftson et al. |
| 6,324,516 | B1 | 11/2001 | Shults et al. |
| 6,438,533 | B1 | 8/2002 | Spackman et al. |
| 6,529,876 | B1 | 3/2003 | Dart et al. |
| 6,542,905 | B1 | 4/2003 | Fogel et al. |
| 6,725,209 | B1 | 4/2004 | Iliff |
| 6,751,630 | B1 * | 6/2004 | Franks et al. ............... 707/102 |
| 6,785,410 | B2 * | 8/2004 | Vining et al. ............... 382/128 |
| 6,868,074 | B1 * | 3/2005 | Hanson ...................... 370/328 |
| 6,915,265 | B1 * | 7/2005 | Johnson ........................ 705/2 |
| 7,233,905 | B1 | 6/2007 | Hutton et al. |
| 2001/0034618 | A1 | 10/2001 | Kessler et al. |
| 2002/0004729 | A1 * | 1/2002 | Zak et al. ....................... 705/3 |
| 2002/0010679 | A1 | 1/2002 | Felsher et al. |
| 2002/0065099 | A1 * | 5/2002 | Bjorndahl ................... 455/553 |
| 2002/0120846 | A1 | 8/2002 | Stewart et al. |
| 2003/0036683 | A1 * | 2/2003 | Kehr et al. .................. 600/300 |
| 2003/0093320 | A1 | 5/2003 | Sullivan |
| 2005/0240613 | A1 | 10/2005 | Logan et al. |

FOREIGN PATENT DOCUMENTS

| | | |
|---|---|---|
| WO | WO 03102726 | 11/2003 |
| WO | WO 03/102726 | 12/2003 |

OTHER PUBLICATIONS

Schriewer, "Airborne Ambulance Saves Precious Time," Tulsa World, May 22, 1996, pp. 1-2.

Hudson, "Attorneys Fear Patient Transfer Claims in Malpractice Cases," Hospitals, Apr. 5, 1991, vol. 65, issue 7, pp. 44-48.

Segroves, "Navigation systems aids medical flights Bad weather landings are now possible at hospitals," News Sentinel, Aug. 7, 1994, pp. D7-8.

Spencer, Thomas, "Contracting for helicopter emergency transport services," Healthcare Financial Management, Aug. 1993, pp. 67-72.

www.aeromed-software.com, Feb. 5, 1998.

Wyoming Medicaid Provider Manual Billing Manuals, Mar. 1, 1999. Section on HCFA 1500, chapters 4 (pp. 4-4, 4-7, and 4-54 in particular) and 9 (pp. 9-11 to 9-13). Section on Transportation, chapter 3 (3-12 to 3-22 in particular) and Appendices (C, D).

EPO Search Report.

Obertots "Report on EMS Software Providers: Interfacing Modules: The Industry Standard" *ThinkThrough Tools, LLC*, Jul. 2007, 9 pages.

SweetTalk Newsletter, *Sweet Computer Services Inc.* vol. 2(3), Aug. 1993, 10 pages.

Various *Sweet Computer Services, Inc.'s* advertisements and brochures for SweetSoft™ software, 1990, 21 pages.

*Lancet Technology, Inc.* "Rescue One, The Complete EMS Database Management Solution" Brochure, 8 pages.

*Flightstar*. "A System Designed for Dispatchers, By Dispatchers" Flyer, 2 pages.

*Computing Technologies for Aviation, Inc.'s* Medical Air Transport System fact sheet, Sep. 1992, 2 pages.

*Droege Computing Services, Inc.* "Computing Services Emergency Flight System", Handout, 1 page.

*EMS Consultants Ltd.* "The Ultimate in EMS Software", Brochure, 30 pages.

EMS Expert @P-Docs Flyer, 2 pages.

*Westech System* brochure, 7 pages.

*LifeLink III* reports, printed Sep. 6, 1988, 14 pages.

*Arec Data Management Systems* Flyer, 3 pages.

*Iris* Product and Services Handout, 2 pages.

*DataWest's* Air-Ops Version 2.1 Software Manual, 15 pages.

*LiFlex* Computer Aided Dispatch System Flyer, 1991 or prior, 2 pages.

*UCS* Fire Rescue Incident Report, 1994, 10 pages.

*The Northern Virginia Sun* Article, dated May 10, 1993, 2 pages.

*Weekly Business* Article, dated Feb. 14, 1994, 1 page.

*UCS* The EMS Commander Brochure, 8 pages.

*Fireline* Brochure, printed Jul. 20, 2007, 4 pages.

*UCS* Pen Based Solutions for EMS Brochure, 4 pages.

*OuterLink* Web, 4 pages.

*AeroMed Software* Flight Management Module Version 2.2 Reference Manual, revised Nov. 10, 1992, 177 pages.

*AeroMed* Software Dispatch Module Version 2.2 Reference Manual, revised Nov. 10, 1992, 150 pages.

*EmsCharts, Inc.'s* Preliminary Invalidity Contentions, *Golden Hour Data Systems, Inc.* v *emsCharts, Inc. and Softech, LLC*, U.S. District Court for the Eastern Division of Texas, Marshall Division, Civil Action No. 2:06-cv-381-TjW, Aug. 27, 2007, 22 pages.

* cited by examiner

| Medical Condition 610 | Patient Information 620 | Patient Location 630 | Transport To 640 | Transportion Means 650 | ETA 660 |
|---|---|---|---|---|---|
| Apparent Heart Attack | Male, 70, home address, insurance info. | Rural City Hospital | Metro Medical Center | LifeFlight Airmedical | 12:30 p.m. |
| Head Trauma | Female, 35, home address, insurance info. | Fashion Valley Mall | Memorial Hospital | Ambulance | 1:53 p.m. |
| Internal injuries | Male, 12, home address, insurance info. | 123 Maple St. Anytown, USA | Memorial Hospital | LifeFlight Airmedical | 9:15 a.m. |
| ... | | | | | |

INTEGRATED EMERGENCY MEDICAL TRANSPORTION DATABASE AND VIRTUAL PRIVATE NETWORK SYSTEM

RELATED APPLICATION

This application claims priority to U.S. Provisional Application No. 60/246,307, filed Nov. 6, 2000 and titled "INTEGRATED EMERGENCY MEDICAL TRANSPORATION DATABASE SYSTEM WITH VIRTUAL PRIVATE NETWORK AS AN APPLICATION SERVICE PROVIDER," which is hereby incorporated by reference in its entirety. This application is related to U.S. application Ser. No. 10/007,664 entitled "DATA ACCURACY FILTER FOR INTEGRATED EMERGENCY MEDICAL TRANSPORTATION DATABASE SYSTEM," filed on even date herewith and having U.S. application Ser. No. 10/007,641 entitled "COMPLIANCE AUDIT FOR INTEGRATED EMERGENCY MEDICAL TRANSPORTATION DATABASE SYSTEM," filed on even date herewith and having U.S. application Ser. No. 60/246,263, entitled "BILLING MODIFIER MODULE FOR INTEGRATED EMERGENCY MEDICAL TRANSPORTATION DATABASE SYSTEM," filed on even date herewith.

BACKGROUND OF THE INVENTION

1. Field of the Invention

This invention relates to an integrated medical database system. More specifically, this invention relates to providing secure communications and user authorization for a medical database in the emergency medical transportation industry.

2. Description of the Related Technology

Current documentation procedures in the air medical transport industry are based on an inefficient paper and pencil technology. Important information is frequently collected on loose sheets of paper. In the environment of emergency medical transport, little time is available to neatly chart and document all pertinent and required information on a single document. Dispatch data, demographic data and clinical data are normally tracked as fragmented pieces of information, which are later coalesced into a complete patient chart. In many cases, these data include the same information, thus forcing the input of redundant information. The resultant chart is therefore vulnerable to being incomplete and unreliable. In a medical setting, incomplete information can lead to disastrous clinical results.

This same technology is used to support industry quality improvement and billing procedures and submit letters of transport justification. This paperwork is usually carried out at a later date, prolonging account receivable times in many instances to the point of compromising and jeopardizing service compensation. Inventory stocking and tracking is similarly a victim of extended turnover times and is often incomplete and inaccurate.

The fragmentation throughout the medical transport environment is also evident in the myriad of entities throughout the country practicing different standards of care and documentation. As is the case in other segments of the healthcare industry, even seemingly simple tasks of communicating among the various entities, as well as among sections of a single providing entity, is severely hampered by the lack of a common communication format. This is especially evident when certain aspects of the system (such as computerized clinical laboratory result displays) have been upgraded with a uniquely tailored computerized system, while the remaining functions are still performed in an archaic manner. While the upgraded system may be effective for one singular aspect, such as dispatching, lab reporting, or chart dictating, the remainder of the system does not improve its effectiveness due to the other archaic components.

In addition, current air medical transport services often transfer data in unsecure protocols and over unsecure public communication paths, and do not always validate users as being authorized users. Thus, current systems are susceptible to unauthorized users gaining access to the system and thereby compromising the integrity and confidentiality of the stored data, as well as the interception or corruption of data in transit via public communications networks, for example the Internet.

Therefore, a comprehensive system exists that includes modules for dispatching emergency medical teams, tracking their movement to and from the accident scene, managing a clinical diagnosis and treatment and accurately billing the patient for the services rendered. Such a system should optionally incorporate security and user authorization measures to ensure the integrity and confidentiality of the data that is transferred over public communications networks and data that is stored by the system. The system should also comply with applicable governmental regulations, for example the federal Health Insurance Portability and Accountability Act of 1996 ("HIPAA"), and future versions of these regulations.

SUMMARY OF CERTAIN INVENTIVE ASPECTS

One aspect of the invention provides a secure integrated emergency medical transportation database system, comprising a medical emergency database comprising at least clinical encounter information, patient demographic data and transport information, a billing module configured to access the medical emergency database and generate a bill for each medical emergency, and a virtual private network configured to allow secure access to the medical emergency database and/or billing module by a plurality of authorized users via a public network, wherein the secure access is compliant with federal regulations. Further provided is a secure integrated emergency medical transportation database system wherein the virtual private network is additionally configured to allow the secure transfer of medical data via the public network. Further provided is a secure integrated emergency medical transportation database system wherein the federal regulations includes the Health Insurance Portability and Accountability Act of 1996 ("HIPAA").

Another aspect of the invention provides a method of providing access to a secure integrated emergency medical transportation database system, comprising collecting at least clinical encounter information, patient demographic data and transport information into a medical emergency database, accessing the medical emergency database, generating a bill for each medical emergency accessed, and securing access to the medical emergency database and/or billing information by a plurality of authorized users via a public network, wherein securing access is compliant with federal regulations. Further provided is a method of providing access to a secure integrated emergency medical transportation database system comprising securing the transfer of medical data via the public network. Further provided is a method of providing access to a secure integrated emergency medical transportation database system wherein the federal regulations includes the Health Insurance Portability and Accountability Act of 1996.

BRIEF DESCRIPTION OF THE DRAWINGS

The above and other aspects, features and advantages of the invention will be better understood by referring to the following detailed description, which should be read in conjunction with the accompanying drawings. These drawings and the associated description are provided to illustrate certain embodiments of the invention, and not to limit the scope of the invention.

FIG. 6 is a diagram of one example of a database configuration layout in accordance with one embodiment of the medical database system.

DETAILED DESCRIPTION OF CERTAIN EMBODIMENTS

Figure 1:
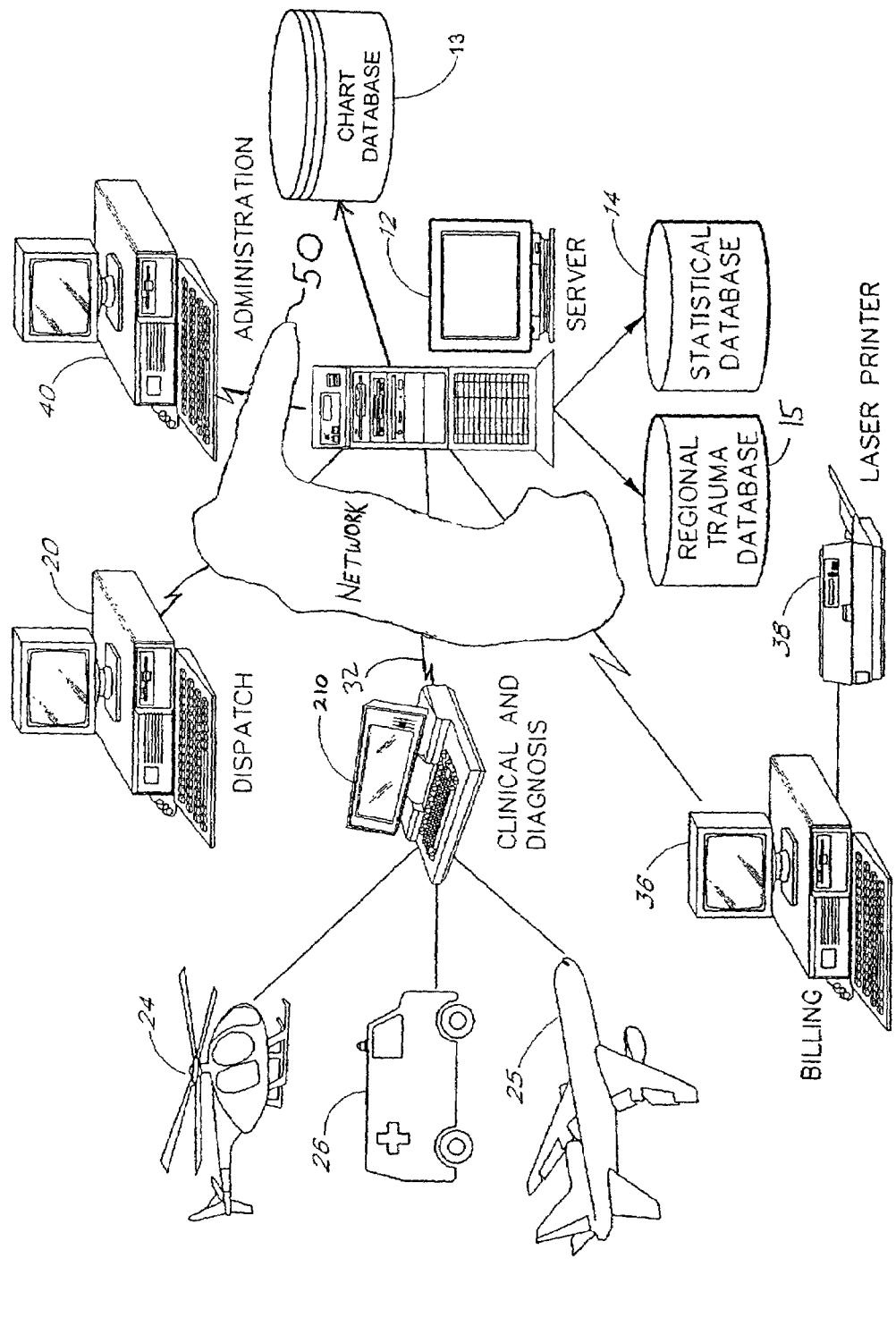
FIG. 1 is a diagram of an on-line computing environment of a medical database system in which a Virtual Private Network ("VPN") may operate in accordance with one embodiment of the present invention.

The following detailed description of certain embodiments presents various descriptions of specific embodiments of the present invention. However, the present invention can be embodied in a multitude of different ways as defined and covered by the claims. In this description, reference is made to the drawings wherein like parts are designated with like numerals throughout.

In certain embodiments, the present invention relates to an object oriented, interactive, international, client-server service for the medical transport industry. The service may integrate all aspects of patient record documentation into a single complete electronic chart. A server computer provides chart database information access to multiple transport providers simultaneously by securely transmitting, storing and maintaining standardized patient data, for instance, using guidelines set forth by the Scrambling Standards Organization. Individual transport-providing entities, such as helicopter and ambulance companies, obtain coded access to this server via phone lines with a modem-equipped personal computer. Security is maintained by assigning each entity a unique code or identifier. Integrated Services Digital Network ("ISDN") lines, Digital Satellite Systems ("DSS"), dedicated trunk lines (for example T1, T3), cable modems, digital subscriber lines ("DSL"), or digital wireless systems may also be used for communication. Such an emergency medical transportation database system is described in U.S. Pat. No. 6,117,073, which is hereby incorporated by reference in its entirety.

Each crew member involved in the patient's chart documentation, i.e. dispatcher, flight nurse, paramedic and physician, as well as administrator and collector, possess coded access to chart portions relevant to their responsibilities and level of care provided. The chart is then electronically generated from the compendium of the information entered in a standardized fashion and in accordance with minimum industry documentation requirements and the inventory of financial health care standards. The system provides complete and accurate chart documentation and maintains internal consistency between each separate module. Furthermore, any sentinel events are automatically referred to the appropriate, responsible party. A sentinel event is any action during the encounter that might require a further review. Examples of sentinel events are scene times exceeding 40 minutes, nonsensical data entry by an emergency transport crew member, supply shortages for equipment not utilized or repeated claim denials.

Billing can be submitted electronically to the appropriate party in an appropriate format that reduces the accounts receivable times for each patient encounter. Letters of justification are automatically generated as well as follow up letters and utilization review reports. Inventory reports and lists of necessary base supplies and medicines are also electronically updated to appropriate supply centers and administrators. Customized and research reports can also be provided rapidly.

Data security and an automatic backup are provided. Although the chart data is normally made the property of the respective transport service provider, the system can retain non-proprietary data to provide industry benchmarking, quality assurance analysis and clinical research opportunities. Such standardized data collection and documentation will furthermore enable the development of an Emergency Medical Services data library to assist in the justification and legislation of governmental preventive policies for public safety.

The communication of data via a public network would normally be susceptible to being intercepted by unauthorized users. In the medical transportation system, data communicated via the public network may include confidential information such as patient medical records. The present invention includes a Virtual Private Network ("VPN") operating on the public network to ensure confidentiality of the patient data. A system according to the present invention complies with applicable regulations regarding the confidentiality of patient data, for example the Health Insurance Portability and Accountability Act of 1996 ("HIPAA"). The VPN of the emergency medical transportation system may be thought of in terms of a three-tier architecture: 1) the user, 2) the business rules processing, and 3) the database.

FIG. 1 provides an overview of the computer hardware involved in one embodiment of a medical database system 100. In this embodiment, the medical database system 100 includes a server computer 12. The server computer 12 can be based on many microprocessors, such as those manufactured by Intel, Motorola, IBM or other chip manufacturers. The server computer 12 enables rapid simultaneous access to many users of the system. In one embodiment, the server computer 12 is an Intel Pentium III class computer having at least 256 Megabytes of RAM and a 10 gigabyte hard disk drive and a 500 megahertz ("MHz") processing speed. In addition, many other standard or non-standard computers may support various embodiments of the medical database system 100.

The database application may be programmed in, for instance, ACIUS's 4th Dimension language and used in conjunction with the 4D Server and Client program. Also, another alternative computer environment is Microsoft Corporation's Visual Basic language with C++ middleware and the BackOffice SQL Server program. It can therefore run in a standard Windows/Macintosh point-and-click office environment, and requires no additional specialized software programming by the user. Additionally, other standard or non-standard computing environments may support embodiments of the medical database system 100.

As illustrated in the embodiment of FIG. 1, the server computer can access a chart database 13. The chart database 13 stores the previously described electronic charts corresponding to patients that have utilized emergency medical transportation. The server computer can also access a statistical database 14 to store and extract statistical information from data entered during patient encounters. The collected statistics might include, for example, average scene and transport times, number of transport requests per demographic region and time of year, average number of advanced procedures performed by crew members and number of complications encountered. In addition, the database 14 can hold information relating to the average length of time to process claims by category and payment plan.

The server computer 12 can also be linked to a regional trauma database 15. The database 15 stores information relating to, for example, local trauma centers, emergency medical practice, and other local trauma-related information.

The dispatch module on the server computer 12 can be accessed via an interface to a dispatch computer 20, which might reside, for example, at the dispatch center that receives the initial call to deploy an emergency medical team. The dispatch computer 20 may provide a communications interface to the server computer 12 so that it acts as computer terminal, or it may contain a portion of the dispatch module.

Based on the scene location and needs of the patient, the dispatch center might deploy, for example, a helicopter 24, airplane 25 or ambulance 26. The dispatch computer 20 communicates with software applications for collecting information on the patient encounter and scheduling and deploying a crew to assist the injured patient. Within one embodiment of the medical database system 100, the helicopter 24, airplane 25 or ambulance 26 would include a portable computing device ("user device") 210 that is used by the emergency medical team during the patient encounter. A wireless connection 32 can be made by the user device 210 to the server computer 12, via a public network 50, for example the Internet, a Wide Area Network (WAN), or an Intranet, to update the database 14 after data is entered. The user device 210 may include clinical and diagnosis modules to assist the emergency medical team in treating the injured patient, or may act as a terminal device to communicate with these modules on the server computer 12. The clinical and diagnosis modules assist the emergency medical team in determining the proper diagnosis and treatment of the patient.

One embodiment of the medical database system 100 may also include a billing computer 36 in communication with the server computer 12 via a public network 50, for example the Internet. The billing computer 36 interfaces with the server computer 12 to run the billing module for tracking inventory. The billing module can be stored directly on the billing computer 36 or, alternatively, stored on the server computer 12 and accessed via the billing computer 36 over the public network 50. The billing module may be used to track inventory and medical equipment. In addition, it may be used during the patient encounter for providing billing functions within the medical database system 100. The billing computer 36 may additionally communicate with a printing device 38, for example an inkjet printer, laser printer, dot matrix printer, or other printing device, to provide printed reports and bills to hospitals, patients and medical centers.

An administration computer 40 communicates with the server computer 12 via the public network 50 to provide administrative reports. These reports relate to the statistical information stored in the statistical database 14. In addition, the administration computer 40 can run reports that relate to payroll, inventory, flight training, or many other administrative issues.

It should be noted that the dispatch computer 20, user device 210, and billing computer 36 can communicate with the server computer 12 through a variety of communications modes and protocols. For example, a wireless Local Area Network ("LAN") or cellular network may connect the various computers with one another. In another embodiment, dedicated or dial-up phone lines may be used to communicate between the different computers.

Figure 2:
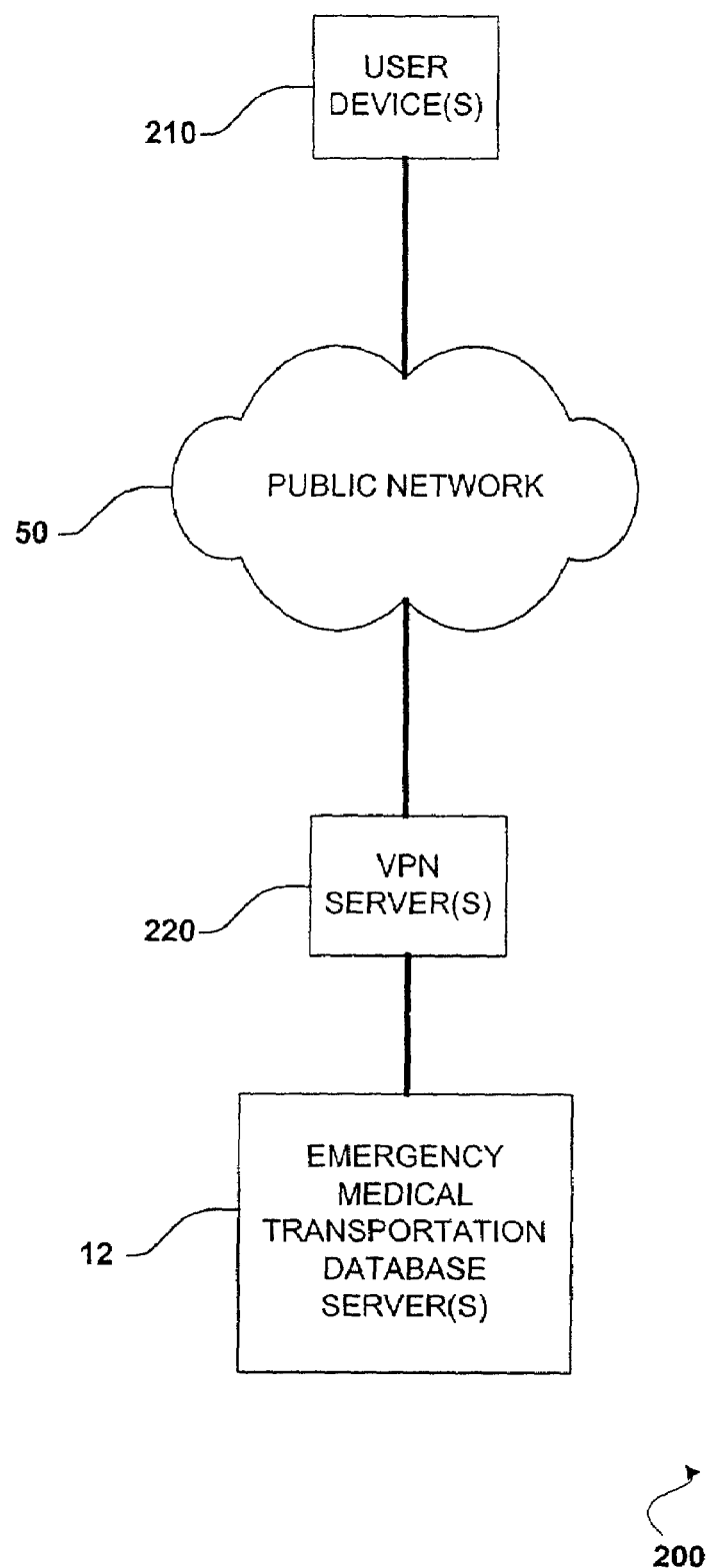
FIG. 2 is a diagram of top-level VPN system components in accordance with one embodiment of the medical database system of FIG. 1.

FIG. 2 is a diagram of top-level VPN system components 200 in accordance with one embodiment of the medical database system 100 of FIG. 1. As described in further detail below in relation to FIG. 3, the user device 210 may consist of one or more types of portable computing device configured to communicate via various communications modes and protocols. In the embodiment of FIG. 2, the user device 210 is configured to communicate over a public network 50, one example being the Internet. The public network 50 enables the user device 210 to communicate with one or more VPN server 220 for logging in and accessing the one or more database servers 12 of the medical database system 100. The logging in and accessing of the database servers 12 is described in further detail below in relation to FIG. 3.

As used herein, the VPN server 220 enables a secure and encrypted communications link between certain nodes on the public network 50. While the nodes can communicate with each other, it is virtually impossible for other nodes to decipher the meaning of the signals or send signals that are believed to be authentic. One secure communications technology that facilitates such a VPN is Secure Sockets Layer ("SSL"). Other secure communications technologies may be used as well, and although SSL is a transport protocol, other security techniques that are not transport protocols may be utilized. The non-SSL techniques may be such that it will quickly and efficiently encrypt and likewise decrypt the data that is being transmitted via the public network 50. Thus, data security and user authentication does not require an expensive and geographically limited dedicated private network, but may be accomplished utilizing VPN technology via a public network 50 such as the Internet.

A VPN server refers to software, hardware, or both that secure network communications and authenticate validity of users in such a way as to minimize the possibility that it can altered or inappropriately viewed or transmitted. A VPN can operate between a number of internet-enabled devices. For example, a VPN can run on two or more computers that are connected together using security technologies such as SSL. In another embodiment, a VPN can operate between a client computer and a server computer using security technologies. In yet another embodiment, a VPN can additionally operate between many client computers and/or many server computers. Many types of portable devices can be used as user devices 210 as part of the VPN as well, as described in further detail below in relation to FIG. 3.

Figure 3:
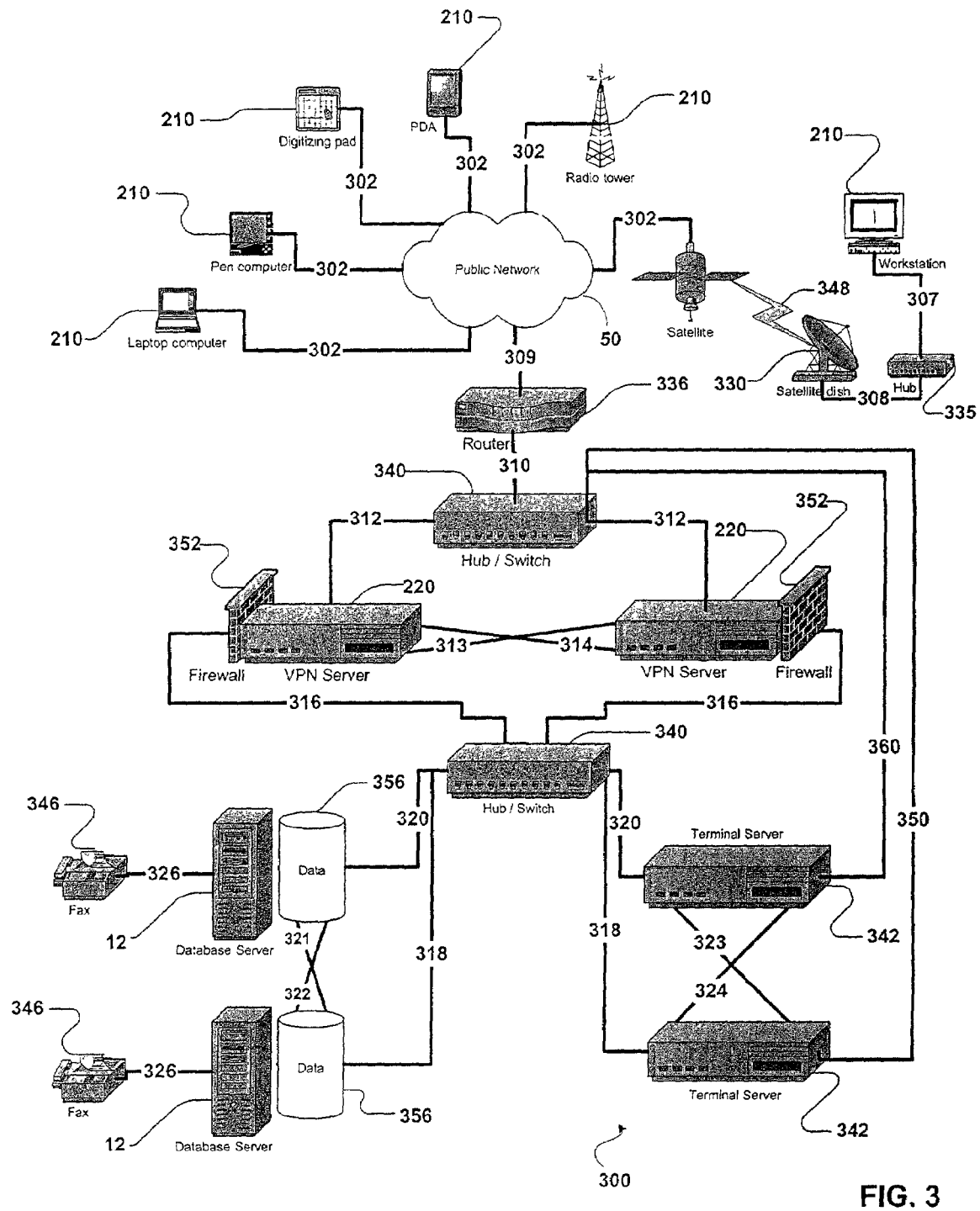
FIG. 3 is a diagram of detailed VPN system components in accordance with the medical database system embodiment of FIGS. 1 and 2.

FIG. 3 is a diagram of detailed VPN system components 300 in accordance with the medical database system 100 embodiment of FIGS. 1 and 2. As shown in FIG. 3, many user devices 210 and modes of data communication 302 may be used to transfer data from the transporting vehicle (see part numbers 24, 25 and 26 in FIG. 1) to/from the medical database system 100 via the public network 50. A non-exhaustive list of user devices 210 that may be used include a laptop computer, a pen computer, a digitizing pad, a personal digital assistant ("PDA"), a wireless device communicating via radio frequency ("RF") waves with a radio tower or a satellite, or a computer communicating with a satellite via a hub 335 and a satellite dish 330.

In the embodiment of FIG. 3, the user devices 210 may communicate via the public network 50 utilizing a number of various modes and protocols of communication 302. For example, such modes of communication 302 include a Universal Serial Bus ("USB"), Firewire, Infrared signals, Bluetooth wireless communications, IEEE 802.2 signals, radio frequency signals such as those of frequency 900 megahertz or higher, straight-through and crossover Ethernet cables, switched packets or sockets transmission, token rings, frame relays, T-1 lines, DS connections, fiber optic connections, RJ-45 and RJ-11 connections, serial pin connections, ultrasonic frequency connections, and satellite communications. Other modes and protocols of communication 302 are also possible and are within the scope of the present invention.

In one embodiment, the user device 210 communicates via the public network 50 with a network communications routing device ("router") 336, for example a main gateway router, which directs network traffic between the appropriate network servers. Examples of commercially available network routers 336 include those made by Cisco, Linksys, Netgear, Netopia, and Hewlett-Packard. The data communications from the user device 210 are directed by the router 336 to the medical database system 100 via a network hub or switch 340. The hub or switch 340 forwards the data communication packets to one or more VPN server 220.

Current technologies that offer VPN server 220 capabilities include hardware, software, and a combination of hardware and software that function both independently and together with other VPN servers 220. In the embodiment of FIG. 3, two VPN servers 220 or shown as an example, but other embodiments may include one VPN server 220, while still other embodiments may include more than two VPN servers 220. Vendors may package VPN capabilities into a device termed an "appliance," which is typically a dedicated hardware device configured with embedded security policies. VPN vendors and manufacturers include, for example, Nortel, Checkpoint, Nokia, Sun Microsystems, Cisco, Netopia, Compaq, IBM, Hewlett-Packard, Watchguard, Linksys, Netgear, and Lucent. Such VPN systems provide system administrators the ability to set security policies and rules as to the rights each user and each application will be allowed on the servers of the medical database system.

In one embodiment, the VPN servers 220 provide encryption and decryption keys to a user, so that the user's data communications are secured using various encryption/decryption algorithms, including, for example, DES, 3DES, MD5, SHA, 40-bit, 56-bit, 128-bit, 168-bit, and other types of encryption/decryption algorithms. In this way, the user establishes a secure communication to the servers of the medical database system 100, using one or a redundant array of VPN servers 220. Further, to increase system up time and reliability, a fail-safe protocol can be implemented to achieve a fail over configuration by connecting redundant communications 313, 314. In such a configuration of VPN servers 220, if one VPN server 220 fails one or more of the other VPN servers 220 undertakes the workload, so that the user is likely not even aware that a failure has occurred.

One or more firewalls 352 may be configured in order to secure the connection beyond the router 336 by preventing external network access to the servers comprising the medical database system 100 by non-authorized devices and/or users on the public network 50. The firewalls 352 may be a separate hardware device, or may be either hardware and/or software that is incorporated into the VPN servers 220. The VPN servers 220 authenticate the users that login to the medical database system 100 and allow only those authorized users access to the medical database system 100 servers through the firewalls 352.

Data communications that the firewalls 352 in conjunction with the VPN server 220 allow to pass through to the servers of the medical database system 100 are forwarded by a hub or switch device 340 to either a terminal server 342 or to a database server 12. The embodiment of FIG. 3 shows two terminal servers 342 and two database server 12, but more or fewer terminal servers 342 and more or fewer database servers 12 may also be used in further embodiments. In addition, the number of terminal servers 342 may be different than the number of database servers 12 in certain embodiments. The terminal servers 342 and/or database servers 12 may be configured as a server farm. A server farm refers to a pool or multitude of servers functioning together to perform common server functionality. In one embodiment, an authorized user may initiate two types of connections to the medical database system 100, a terminal server request or a direct database server request. Such server farms are able to perform load balancing or fail-safe switching of servers should one or more become non-operational to accomplish redundancy or system efficiency.

In one embodiment, a direct database server request may be made by the user to connect the user device 210 to the database server 12. The database 356 and database server 12 operate in a client/server relationship, such that in order to access the database, the user establishes a client connection to the database server 12. Database 356 access is accomplished by making database requests to the database server 12 over a secure, password protected, and dedicated channel of communication. In cases where the communications channel supports a direct connection, i.e. low communications latency, sufficient data communication bandwidth, or strong system configuration, the user devices 210 can communicate directly with the database servers 12.

The database 356 and database server 12 contain the operating system components to run the core system, for example, Macintosh, Windows, Linux, Unix, and other operating systems. In one embodiment of the medical database system 100, the database server 12 and database 356 utilize a database that is ODBC, Sequel, Sybase, 4D, and Oracle compliant such that it can integrate with a majority of these operating systems and other database systems. The data may be stored on a main database server 12, but may also be configured to mirror and fail-safe over to another database system, achieving redundancy, system efficiency, and backup efficiency, among other benefits.

Current database 356 technologies include commercially available brand and product names, for example, Oracle, 4D, Sequel Server, Sybase, Filemaker, Access, Cold Fusion, FoxPro, and other database systems. Such databases function as relational databases that allow for querying and database development on multiple planes, and also for granting user specific access to regions of the database. These databases also typically include client software applications that communicate with the database 356. The client software applications are installed on the user workstation and create a channel of communication with the user and the database 356.

However, in other cases, the communications channel does not support a direct connection, so the user device 210 communicates with the database servers 12 through the terminal servers 342. A terminal server request may be made by the user to connect the user device 210 to the terminal server 342, such that the terminal servers 342 deliver a screen to the user to control a remote server. The terminal servers 342 allow multiple users to connect to run a heterogeneous portfolio of applications, providing the user with what appears to be a personal and individual work session. Thus, the user may remotely control the terminal servers 342 to perform the communications processing with the database servers 12 as described above. The terminal server 342 may be many various types of devices running various types of operating systems, for example Microsoft servers, Unix servers, BSD, Apple Macintosh, Linux, and other computer systems and operating systems. Some examples of common enterprise level software platforms in current existence and use include, for example, Microsoft Terminal Services using the Remote Desktop Protocol ("RDP"), Cisco PIX Firewalls, PCAnywhere, Timbuktu, VNC, and Citrix Metaframe software applications. In a further embodiment, a fax machine 346 may optionally be connected to the database servers 12, enabling the database servers 12 to send faxes, for example, when a paper invoice is required to be sent.

Figure 4:
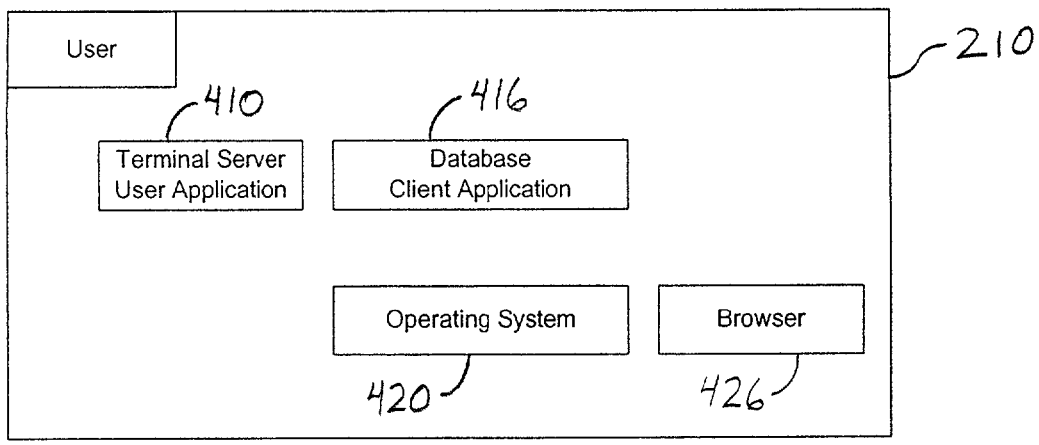
FIG. 4 is a block diagram of client applications of the user device, VPN server, and terminal server components as shown in the embodiment of FIG. 3.
Figure 4:
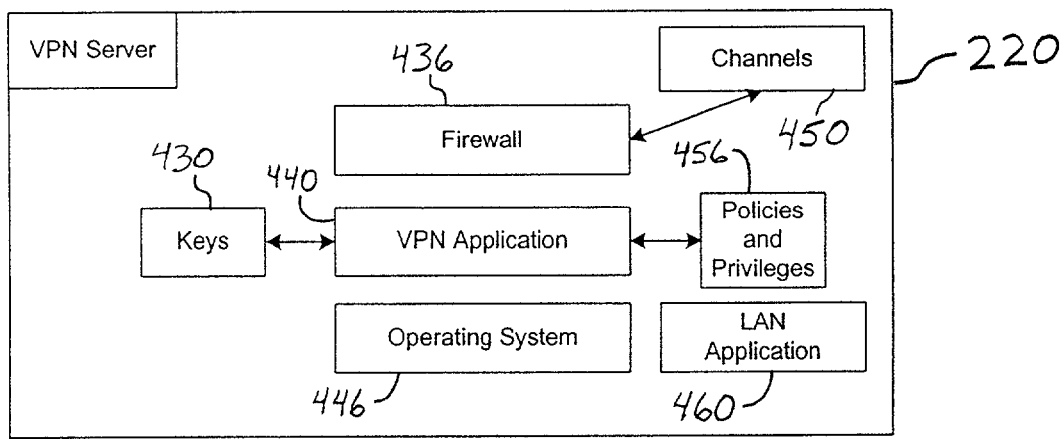
Figure 4:
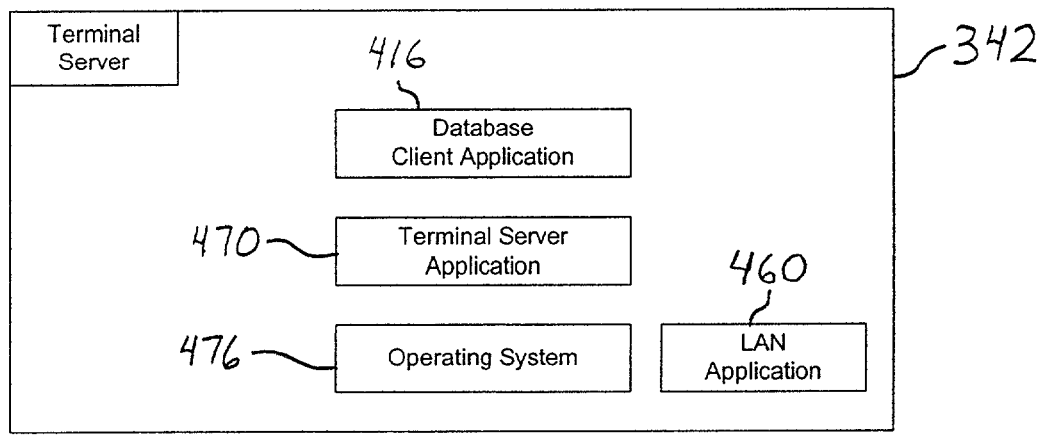

FIG. 4 is a block diagram of client applications of the user device 210, VPN server 220, and terminal server 342 components as shown in the embodiment of FIG. 3. In this embodiment, the user devices 210 include client applications for the terminal server user application 410 and database client application 416. As described above in relation to FIG. 3 and below in relation to FIG. 5, one embodiment of the user devices 210 only includes one or the other of the terminal server user application 410 and database client application 416, depending on whether the user connects to the database servers 12 directly or connects through the terminal servers 342. However, other embodiments may include both of these applications 410, 416. In one embodiment, the database client application 416 is the Citrix client Metaframe, or it may additionally be Nfuse, which allows the use of a web browser.

The user devices 210 additionally include operating system software 420, for example Macintosh, Windows, Linux, Unix, or other computer operating systems. The user devices 210 may additionally include a browser application 426 for accessing the public network 50 such as the Internet and allowing the display of and interaction with various websites accessible via the Internet. For example, several such commonly used browser applications are Microsoft Internet Explorer and Netscape Navigator.

In the embodiment of FIG. 4, the VPN servers 220 include client applications for the firewall 436 and VPN applications 440, which may both be provided by a single application, for example Checkpoint VPN1. The VPN application 440 utilizes encryption keys 430 and is controlled by policies and privileges 456 that are set up by someone with system administrator level privileges. For example, the policies and privileges 456 include specifying which ports are authorized to send data in what direction (e.g., input, output, or both), and specifying which applications are authorized to access which ports. The VPN servers 220 additionally include operating system software 446, as described above in relation to the user device 210 of FIG. 4. The VPN servers 220 additionally include Local Area Network ("LAN") application software 460, for example TCP/IP, UDP, IPS/SPX, NetBeui, NetBios, XML, and AppleTalk, for file sharing, printing, internal server communications, and other LAN network capabilities.

In one embodiment, the terminal servers 342 include the database client application 416 as described above in relation to the user device 210 of FIG. 4. The terminal servers 342 additionally include a terminal server application 470, an operating system software 476 as described above in relation to the user device 210 of FIG. 4, and the LAN application 460 as described above in relation to the VPN server 220 of FIG. 4.

While the embodiment of FIG. 4 shows a specific example of the client applications that may be included in the user devices 210, VPN servers 220, and terminal servers 342, other embodiments utilizing other client applications in various configurations are also within the scope of the present invention. As FIG. 4 illustrates one embodiment of the devices and servers of the medical database system 100, the present invention is not limited to this embodiment but also includes other embodiments as well.

Figure 5:
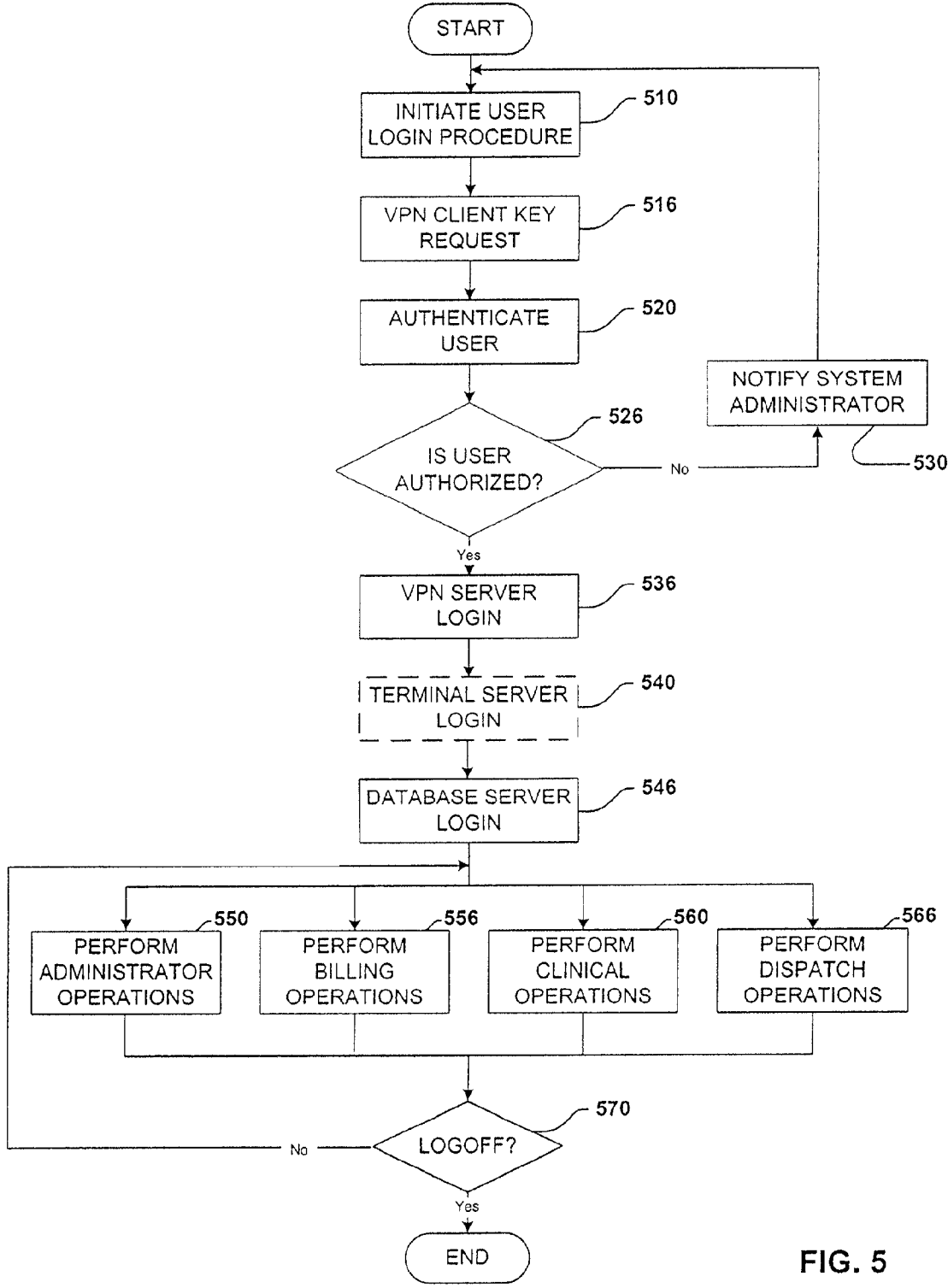
FIG. 5 is a flowchart of database access operations of the medical database system in accordance with the embodiments of FIGS. 1-3.

FIG. 5 is a flowchart of database access operations of the medical database system 100 in accordance with the embodiments of FIGS. 1-3. At stage 510, the user initiates the login connection for a VPN client key. At stage 516, the VPN client key request is tagged and encapsulated with information and sent for authentication within the VPN server 220. The VPN server 220 includes a decision process mechanism for funneling applications and users to the predetermined authorized areas within the public network 50. The VPN server 220 additionally blocks those activities that are not authorized within the policies as set by the system administrator. Another function of the VPN server 220 is to make the user authentication determination shown at stage 520. At decision stage 526, the system either allows successful access to the database system, or denies access to the requesting user. Upon such a denial of access, at stage 530 the system administrator is optionally notified of the denial of access to the user. The system may utilize a variety of ways of notifying the system administrator, such as via paging, fax, email, audio/visual alerts, entry into a log file, or other ways of notification. The user may attempt the login and authentication process again at stage 510.

If the user authentication at stage 526 is instead successful, the user is notified of successful VPN access. A notification may additionally be sent to the system administrator, for example, via email, fax, audio/visual alerts, log file entry, or other notification means. At stage 536, the user logs in to the VPN server 220 and further communications utilize a dedicated, secure, and encrypted channel. Private VPN level connections are designed and configured with a high level of security and encryption to maintain data confidentiality. The VPN encapsulates the data and creates encryption around each packet of information with a variety of different encryption schemes that are enforced by the database server 12 and the database 356. In the current technology, standard encryption uses 40 bit, 56 bit, 128 bit, and 168 bit keys. Trends in the technology indicate that in the future these degrees of encryption will be enhanced, or may possibly use a combination of levels to maximize efficiency and encoding.

At optional stage 540, the user may log in to the terminal server 342 to communicate with the database server 12 via the terminal server 342. However, at stage 546 the user may also elect to log in directly to the database server 12 and bypass the terminal server login at stage 540. Having logged in to the database server 12, the database server 12 determines, based on the authentication level, the access that the user will be allowed, which in turn governs which of the following operations the user may perform. At stage 550 the user may elect to perform administrator operations, assuming the user has the required authentication level. At stage 556 the user may elect to perform billing operations, again assuming the user has the required authentication level. At stage 560 the user may elect to perform clinical operations, assuming the user has the required authentication level. At stage 566 the user may elect to perform dispatch operations, once again assuming the user has the required authentication level. In other embodiments, the users may elect to perform other medical database system operations they are authorized to perform that are not shown in the embodiment of FIG. 5.

At decision stage 570, the user may elect to log off the medical database system 100 and end the operations shown in FIG. 5, or alternatively the user may elect to remain logged in to the system and elect another operation to perform.

FIG. 6 is a diagram of one example of a database configuration layout 600 in accordance with an embodiment of the medical database system 100. In this embodiment, a medical database record, which may be stored in the chart database 13 shown in FIG. 1, includes fields for medical condition 610, patient information 620, patient location 630, transportation destination 640, means of transportation 650, and estimated time of arrival ("ETA") 660. In other embodiments, the medical records may include more or fewer fields than are shown in the embodiment of FIG. 6. In addition, the databases may include more or fewer record entries than shown in the embodiment of FIG. 6.

The database configuration layout 600 example shown in FIG. 6 may contain confidential patient medical information. Such database records are securely transferred between the database 356 and the various servers of the medical database system 100 as described above in relation to the VPN system in FIGS. 3 and 5. The patient information is essentially safe from interception by unauthorized users on the public network 50 in a system as described herein.

While the above detailed description has shown, described, and pointed out novel features of the invention as applied to various embodiments, it will be understood that various omissions, substitutions, and changes in the form and details of the device or process illustrated may be made by those skilled in the technology without departing from the spirit of the invention. The scope of the invention is indicated by the appended claims rather than by the foregoing description. All changes that come within the meaning and range of equivalency of the claims are to be embraced within their scope.

What is claimed is:

1. A secure integrated emergency medical transportation database system for use in a computing environment having a processor and a data storage, the system comprising:
   a medical emergency database stored in the data storage and accessible by the processor, wherein the database comprises at least clinical encounter information, patient demographic data and transport information comprising at least vehicle path tracking information, as electronic protected health information for a plurality of medical emergency incidents requiring transport and a plurality of patients;
   a billing module being executable by the processor and configured to access the medical emergency database and generate a bill for each medical emergency requiring transport wherein the bill includes at least portions of each of the patient demographic data, the clinical information, and the transport information; and
   a secure communications application being executable by the processor and configured to allow a plurality of authorized users to connect to the system via a public network and further configured to allow secure access to the medical emergency database and/or billing module by the plurality of authorized users via the public network,
   wherein the secure access comprises technical security measures to protect against unauthorized access to the electronic protected health information during transmission over the public network, for secure storage of data indicative of a medical emergency in the medical emergency database, from a location in the field that is remote from a health service facility.

2. The system of claim 1, wherein the secure communications application is additionally configured to allow the secure transfer of medical data via the public network.

3. The system of claim 1, wherein the secure access is compliant with the Health Insurance Portability and Accountability Act of 1996 in the form as enacted.

4. The system of claim 1, wherein the secure access protects against a risk of interception during electronic transmission of the health information.

5. The system of claim 1, wherein the secure access is compliant with federal regulations including the associated Code of Federal Regulations Title 45 Parts 160 and 164 in its form as originally implemented.

6. The system of claim 1, wherein the secure communications application uses secure sockets layer.

7. The system of claim 1, wherein the secure communications application includes a virtual private network.

8. The system of claim 1, wherein the secure communications application includes encryption and decryption algorithms.

9. The system of claim 1, wherein the secure communications application includes encryption and decryption keys.

10. The system of claim 1, wherein the secure communications application authenticates validity of a one of the plurality of authorized users.

11. The system of claim 1, wherein the secure communications application includes a dedicated, secure and encrypted channel.

12. The system of claim 1, wherein the transport information comprises information obtained about the transport after first contact by medical transport personnel.

13. The system of claim 12, wherein the transport information is wirelessly communicated to the emergency medical database from a location remote from the medical emergency database.

14. The system of claim 1, wherein the transport information is associated with the clinical encounter information by at least patient pickup data in the emergency medical database.

15. The system of claim 1, additionally comprising a portable computing device used by emergency medical personnel to wirelessly access a public network in real time while at the patient pick-up location or during a transport of an emergency medical services patient.

16. The system of claim 15, wherein the secure communication application is associated with the computing device.

17. The system of claim 15, wherein the portable computing device is used by emergency medical personnel inside an emergency transport vehicle.

18. The system of claim 1, wherein the technical security measures minimize access to inappropriate information based on job requirements.

19. The system of claim 1, wherein the field location is at a location between two health service facilities that are the source and destination of the transport.

20. The system of claim 1, wherein the secure communications application comprises a virtual private network (VPN) interface which allows encryption of all transmitted data as well as the encryption of authorization codes.

21. The system of claim 20, wherein the VPN interface comprises processing rules that encapsulate and create encryption around each packet of information which is transmitted.

22. The system of claim 20, wherein the VPN interface comprises the ability to set policies and rights regarding access on an individual user basis.

23. The system of claim 20, wherein the VPN interface is the only gateway to the medical transportation database.

24. The system of claim 1, further comprising a portable computing device having a wireless communications capability for communicating data indicative of a medical emergency incident from the remote location in the field, for storage in the medical emergency database and a portion of the data be used for billing.

25. The system of claim 1, wherein the authorized users are emergency medical transport personnel from a plurality of transport providers.

26. The system of claim 1, additionally comprising a dispatch module in communication with a dispatch center that dispatches vehicles to the location of the emergency medical incident.

27. The system of claim 1, wherein the transport information is comprised of one of: the flight path of a helicopter, the flight path of an airplane and the route of an ambulance.

28. A method of providing access to a secure integrated emergency medical transportation database including a computing environment having a processor and a data storage, the method comprising:

collecting at least clinical encounter information, patient demographic data and transport information comprising at least vehicle tracking path information, as electronic protected health information for each of a plurality of medical emergency incidents requiring transport into a medical emergency database, wherein the medical emergency database comprises electronic data stored in the data storage and wherein the medical emergency incidents are associated with a plurality of patients;

accessing the medical emergency database via the processor;

generating via the processor a bill for each medical emergency incident accessed wherein the bill includes at least portions of each of the patient demographic data, the clinical information, and the transport information; and securing access to the medical emergency database and/or billing information by a plurality of authorized users via a public network, wherein securing access comprises using technical security measures to protect against unauthorized access to electronic protected health information during transmission over the public network, for secure storage of data indicative of a medical emergency in the medical emergency database from a location in the field that is remote from a health service facility.

29. The method of claim 28, further comprising securing the transfer of medical data via the public network.

30. The method of claim 28, wherein securing access is compliant with the Health Insurance Portability and Accountability Act of 1996 in the form as enacted.

31. The method of claim 28, wherein securing access comprises protecting against a risk of interception during electronic transmission of the health information.

32. The method of claim 28, wherein securing access is compliant with federal regulations including the associated Code of Federal Regulations Title 45 Parts 160 and 164 in its form as originally implemented.

33. The method of claim 28, wherein securing access comprises using secure sockets layer.

34. The method of claim 28, wherein securing access comprises using a virtual private network.

35. The method of claim 28, wherein securing access includes using encryption and decryption algorithms.

36. The method of claim 28, wherein securing access includes using encryption and decryption keys.

37. The method of claim 28, wherein securing access includes authenticating validity of a one of the plurality of authorized users.

38. The method of claim 28, wherein securing access comprises using a dedicated, secure and encrypted channel.

39. The method of claim 28, wherein the transport information comprises patient pickup data used for billing.

40. The method of claim 28, wherein the collecting comprises wirelessly sending the electronic protected health information by emergency medical personnel via a public network while at the scene of the patient encounter or during transport of an emergency medical services patient.

41. The method of claim 40, wherein the wirelessly collecting comprises using a portable computing device inside an emergency transport vehicle.

42. The method of claim 28, wherein the field location is at a location between two health service facilities that are the source and destination of the transport.

43. The method of claim 28, further comprising receiving signals indicative of a medical emergency incident which were originally wirelessly transmitted by a portable computing device having a wireless communications capability.

44. The method of claim 28, wherein the transport information is comprised of one of: the flight path of a helicopter, the flight path of an airplane and the route of an ambulance.

* * * * *